United States Patent
Di Biase et al.

(10) Patent No.: US 11,576,592 B2
(45) Date of Patent: Feb. 14, 2023

(54) METHODS AND SYSTEM FOR CHARACTERISING TREMORS

(71) Applicant: Oxford University Innovation Limited, Oxford (GB)

(72) Inventors: Lazzaro Di Biase, Oxford (GB); John-Stuart Brittain, Oxford (GB); Brown Peter, Oxford (GB); Vincenzo Di Lazzaro, Oxford (GB); Syed Ahmar Shah, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 236 days.

(21) Appl. No.: 16/478,545

(22) PCT Filed: Jan. 17, 2018

(86) PCT No.: PCT/GB2018/050122
§ 371 (c)(1),
(2) Date: Jul. 17, 2019

(87) PCT Pub. No.: WO2018/134579
PCT Pub. Date: Jul. 26, 2018

(65) Prior Publication Data
US 2020/0046259 A1 Feb. 13, 2020

(30) Foreign Application Priority Data
Jan. 17, 2017 (GB) .................................... 1700767

(51) Int. Cl.
*A61B 5/11* (2006.01)
*A61B 5/00* (2006.01)

(52) U.S. Cl.
CPC .......... *A61B 5/1101* (2013.01); *A61B 5/7282* (2013.01)

(58) Field of Classification Search
CPC ........................... A61B 5/7282; A61B 5/1101
(Continued)

(56) References Cited

U.S. PATENT DOCUMENTS 1,889,132 A 11/1932 Peik
5,904,610 A 5/1999 Ciniglio et al.
(Continued)

FOREIGN PATENT DOCUMENTS

BE 1011508 A 10/1999
CN 203993567 U 12/2014
(Continued)

OTHER PUBLICATIONS

Brittain, John-Stuart, et. al. "Distinguishing the Central Drive to Tremor in Parkinson's Disease and Essential Tremor" Jan. 14, 2015, Journal of Neuroscience, 35 (2), 795-806 (Year: 2015).*
(Continued)

*Primary Examiner* — Christian Jang
*Assistant Examiner* — Anna Roberts
(74) *Attorney, Agent, or Firm* — Thomas|Horstemeyer, LLP

(57) ABSTRACT

A method of characterising tremor stability in a subject is described for a subject having an involuntary tremor symptomatic of a neurological disorder. The method comprising: identifying a series of tremor cycles from measured tremor data of the subject, said tremor cycles measuring periodic variation in movement of the subject due to the tremor; determining an instantaneous frequency for each tremor cycle and collating the instantaneous frequencies; determining an instantaneous variation between the instantaneous frequencies of each pair of adjacent tremor cycles within the series; comparing the instantaneous variation to the collation of determined instantaneous frequencies to determine a distribution of instantaneous variations; and determining an
(Continued)

index value of the distribution of the instantaneous variations, said index value defining the stability of the tremor.

18 Claims, 13 Drawing Sheets

(58) Field of Classification Search
USPC .......................................................... 600/595
See application file for complete search history.

(56) References Cited

U.S. PATENT DOCUMENTS

| | | | |
|---|---|---|---|
| 2013/0143473 A1 | 6/2013 | Hibino et al. | |
| 2014/0206970 A1* | 7/2014 | Wesley | G16H 15/00 600/365 |
| 2015/0265205 A1* | 9/2015 | Rosenbek | A61B 5/4803 600/586 |

FOREIGN PATENT DOCUMENTS

| | | |
|---|---|---|
| DE | 4244234 A1 | 6/1994 |
| DE | 19954988 A1 | 5/2001 |
| GB | 2175976 A | 12/1986 |
| JP | H09300220 A | 6/2001 |
| RU | 2558176 C1 | 7/2015 |

OTHER PUBLICATIONS

Norman, Kathleen, et. al. "The measurement of tremor using a velocity transducer: comparison to simultaneous recordings using transducers of displacement, acceleration, and muscle activity" 1999, Journal of Neuroscience Methods, 92, 41-54 (Year: 1999).*
Nistico, et. al. "Synchronous pattern distinguishes resting tremor associated with essential tremor from rest tremor of Parkinson's disease" Jan. 2011, Parkinsonism and Related Disorders, 17 (1), 30-33 (Year: 2011).*
UK Search Report for GB1700767.5, dated Jul. 3, 2017, pp. 1-4.
International Search Report and Written Opinion for PCT/GB2018/050122, dated Mar. 29, 2018, pp. 1-11.
J.S. Brittain et al., "Distinguishing the Central Drive to Tremor in Parkinson's Disease and Essential Tremor", The Journal of Neuroscience: The Official Journal of the Society for Neuroscience, vol. 35, No. 2, Jan. 14, 2015 (Jan. 14, 2015), pp. 795-806.
Lazzaro Di Biase et al., "Tremor stability index: a new tool for differential diagnosis in tremor syndromes", BRAIN., vol. 140, No. 7, Apr. 27, 2017 (Apr. 27, 2017), pp. 1977-1986.

* cited by examiner

METHODS AND SYSTEM FOR CHARACTERISING TREMORS

CROSS-REFERENCE TO RELATED APPLICATIONS

This application is the National Stage of International Application No. PCT/GB2018/050122, filed Jan. 17, 2018, which claims the priority to GB 1700767.5, filed Jan. 17, 2017, which are entirely incorporated herein by reference.

FIELD

Methods and a system of characterising tremors are described. In particular, methods and a system of determining an index value of the distribution of instantaneous variations of the tremor that defines tremor stability are described.

BACKGROUND

Misdiagnosis in tremor syndromes is a common and often underestimated problem. Central to this problem is the lack of accurate diagnostic tools that can distinguish different tremor aetiologies. Indeed, the diagnostic accuracy of Parkinson's disease (PD) has been estimated to be 80% amongst movement disorders experts, and 74% if the disease is diagnosed by a neurologist not expert in movement disorders.

In Essential tremor (ET) there is no gold standard diagnostic procedure, not even at post-mortem, and diagnosis is made purely on clinically defined criteria. 37% of ET patients are misdiagnosed.

The stability of tremor frequency over time has recently been considered as the basis for a potential diagnostic aid in Brittain et al. *The Journal of Neuroscience* 35, 795-806 (2015). This study analysed the variation in instantaneous tremor frequency over time, and showed that, in ET the frequency of tremor remains stable only over a narrow range of frequencies, whereas in Parkinson's disease tremor (PDT) the frequency can remain stable over a much broader range.

In the present disclosure, it is an object to address or at least ameliorate some of these shortcomings.

SUMMARY

According to a first aspect of the present invention, there is provided a method of characterising tremor stability in a subject, said subject having an involuntary tremor symptomatic of a neurological disorder, the method comprising: identifying a series of tremor cycles from measured tremor data of the subject, said tremor cycles measuring periodic variation in movement of the subject due to the tremor; determining an instantaneous frequency for each tremor cycle and collating the instantaneous frequencies; determining an instantaneous variation between the instantaneous frequencies of each pair of adjacent tremor cycles within the series; comparing the instantaneous variation to the collation of determined instantaneous frequencies to determine a distribution of instantaneous variations; and determining an index value of the distribution of the instantaneous variations, said index value defining the stability of the tremor.

The present disclosure provides an index value that is representative of the distribution of the instantaneous variations across all the measured frequencies of the tremor, rather than a subset. This provides an indication of the relative stability of the tremor across the range of observed instantaneous frequencies. One particular problem with traditional attempts to measure tremor is that the frequencies vary apparently at random. However, the present invention instead measures the variations between tremor cycles, with the relative range of variation, described by the index value defining the tremor status of the subject. This tremor status may be further utilised to provide a possible deterministic tool. For example, index values above or below a certain threshold value may be indicative of a particular tremor status.

It is important to note that the index value is determined based on a comparison of the instantaneous variations between the instantaneous frequencies of (each) pair of adjacent tremor cycles. In this way, the determination relies upon the collected and collated data of each subject, rather than a comparison between data from one subject and data from another subject having no tremor. In this case, there is no diagnosis of the underlying condition (namely tremor)—patients known to have tremor instead have their tremors analysed to determine an index value indicative of their tremor status.

Additionally, by undertaking a statistical approach across the whole range of observed frequencies, selection bias can be reduced and bin width issues mitigated.

As noted, each tremor cycle has only one instantaneous frequency, however it can be appreciated that this may shift between cycles.

By analysis of the overall tremor stability characteristics of PDT and ET, the index value (sometimes referred to as a tremor stability index (TSI)), allows for the discrimination of these two tremor types.

In embodiments, the tremor may be obtained using a sensor. The measured tremor data may be obtained by a triaxial accelerometer or a velocity-transducing laser. It can be appreciated that other means for sensing the tremor of a subject may be utilised. The sensing of the tremor may comprise extracting a waveform of the tremor as detected over a set period of time.

In embodiments, the frequency of each tremor cycle may be identified by determining the first principal component of the tremor. The first principal component may be extracted using principal component analysis. The first principal component may be filtered, such as between 2 and 9 Hz frequency. Such filtering may be performed using a high-pass filter, or may be undertaken using a software solution.

The frequency of each tremor cycle may be identified by trend correcting the tremor cycles using a high pass filter.

The instantaneous frequency of each tremor cycle may be identified by determining an instantaneous period for each tremor cycle. In this embodiment, the instantaneous frequency may be equal to the inverse of the instantaneous period.

Accordingly, the instantaneous period may be determined by using a zero crossing threshold on the measured tremor. This threshold crossing data may be used to define each tremor cycle. In particular, the time taken for a tremor cycle to cross the threshold is used to calculate the instantaneous period of that tremor cycle.

The index value may be determined by calculating the interquartile range of the distribution of the instantaneous variations.

In embodiments, the index value may be compared with one or more known reference index values. The reference index values may be generated from subjects having a known tremor status. This allows a comparison between existing clinical data and a subject having an unknown tremor status.

In embodiments, the step of measuring the tremor may comprise the step of: measuring the tremor for a time period. The time period may be between 10s and 100s.

According to a second aspect of the present invention, there is provided a method of determining a tremor status in a subject, said subject having an involuntary tremor symptomatic of a neurological disorder, the method comprising: determining, using the method as described in any embodiment of the first aspect, an index value for the subject, said index value characterising the stability of the tremor; comparing the index value to a database of known index values, said known index values being previously generated from subjects having a known tremor status; and determining the tremor status of the subject based on the index value comparison.

According to a third aspect of the present invention there is provided a method of distinguishing tremor statuses of subjects from a cohort of subjects, said subjects having an involuntary tremor symptomatic of a neurological disorder, the method comprising: determining, using the method of any embodiment of the first aspect, an index value for each subject, said index value characterising the stability of the tremor for each subject; and identifying groupings of subjects based on their index value, wherein the groupings define separate tremor statuses.

According to a fourth aspect of the present invention, there is provided a system for calculating a value indicative of a tremor stability of a subject having an involuntary tremor symptomatic of a neurological disorder, said system comprising: a processor configured to: receive sensor data measuring tremor data of the subject, said tremor data comprising tremor cycles measuring periodic variation in movement of the subject due to the tremor; determine instantaneous frequencies for tremor cycles of the tremor; calculate frequency variations between the tremor cycles; and determine an index value indicative of the distribution of the frequency variations with instantaneous frequency.

The system may further comprise a database containing one or more reference index values generated from subjects having a known tremor status.

The processor may be further configured to compare the index value to the reference index values to determine the tremor status.

According to a fifth aspect of the present invention, there is provided a method of analysing a series of tremor cycles to determine a tremor status, said method comprising the steps of: analysing a tremor series comprising a plurality of tremor cycles; determining an instantaneous frequency for each tremor cycle; determining an instantaneous variation between the instantaneous frequencies of adjacent tremor cycles within the series; comparing the instantaneous variation to the range of determined instantaneous frequencies to determine a distribution of instantaneous variations; and determining an index value of the distribution of the instantaneous variations, said index value defining a tremor status.

According to a sixth aspect of the present invention a method of collecting tremor information from a subject is described. Said subject having an involuntary tremor symptomatic of a neurological disorder, the method comprising: sensing a tremor in the subject; measuring the tremor for a predefined time; identifying a series of tremor cycles from the measured tremor; determining an instantaneous frequency for each tremor cycle and collating the instantaneous frequencies; determining an instantaneous variation between the instantaneous frequencies of each pair of adjacent tremor cycles within the series; comparing the instantaneous variation to the collation of determined instantaneous frequencies to determine a distribution of instantaneous variations; and determining an index value of the distribution of the instantaneous variations.

It can be appreciated that embodiments relevant to any one or more of the first to third aspects may also be applied to the fourth aspect.

There may be provided a computer program, which when run on a computer, causes the computer to configure any apparatus, including a circuit, controller, sensor, filter, or device disclosed herein or perform any method disclosed herein. The computer program may be a software implementation, and the computer may be considered as any appropriate hardware, including a digital signal processor, a microcontroller, and an implementation in read only memory (ROM), erasable programmable read only memory (EPROM) or electronically erasable programmable read only memory (EEPROM), as non-limiting examples. The software implementation may be an assembly program.

The computer program may be provided on a computer readable medium, which may be a physical computer readable medium, such as a disc or a memory device, or may be embodied as a transient signal. Such a transient signal may be a network download, including an internet download.

These and other aspects of the invention will be apparent from, and elucidated with reference to, the embodiments described hereinafter.

BRIEF DESCRIPTION OF DRAWINGS

Embodiments will be described, by way of example only, with reference to the drawings, in which

FIG. 1b illustrates a filtered signal of FIG. 1a;

Figure 1A:
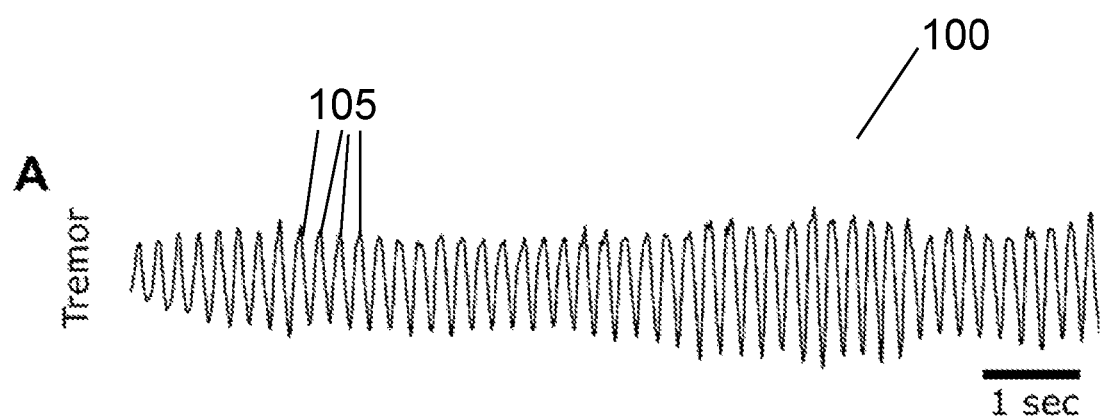
FIG. 1a illustrates a signal representation of a tremor according to an embodiment of the present disclosure.

It should be noted that the figures are diagrammatic and not drawn to scale. Relative dimensions and proportions of parts of these figures have been shown exaggerated or reduced in size, for the sake of clarity and convenience in the drawings. The same reference signs are generally used to refer to corresponding or similar feature in modified and different embodiments.

DETAILED DESCRIPTION OF EMBODIMENTS

Figure 1B:
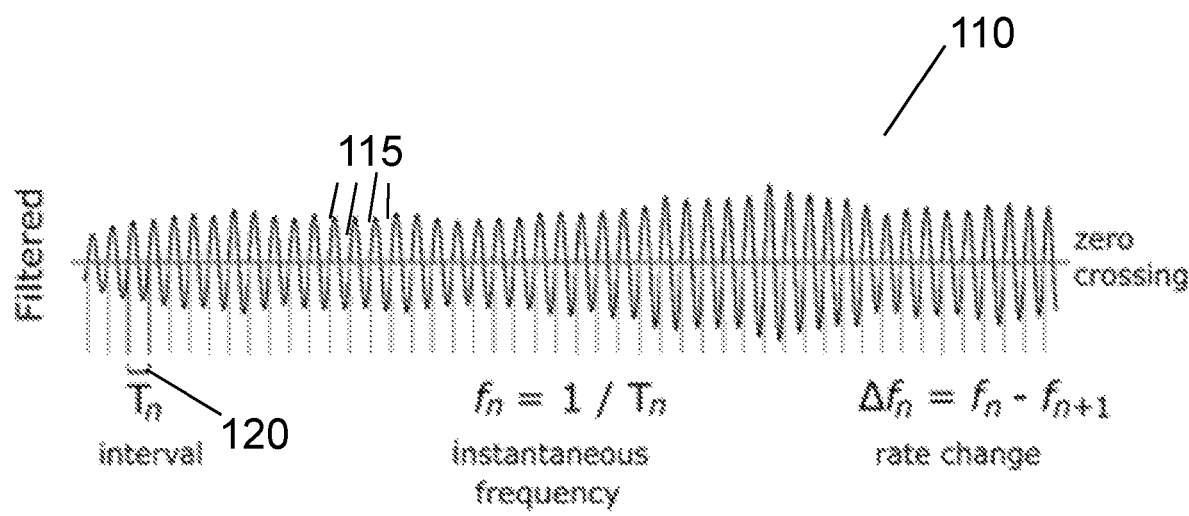

FIGS. 1a and 1b shows the results of a measured tremor 100 from a first cohort of data—the collection of data from various cohorts is described in detail below. In general terms, the tremor data was obtained from subjects experiencing tremor using a sensor, such as a triaxial accelerometer.

The tremor data shows a tremor that has been measured for a predetermined time. A number of tremor cycles are collected within the predetermined time. As shown in FIG. 1, the raw tremor data is first subject to after component analysis to extract the first principal component. In particular, FIG. 1a shows the first principal component of a hand tremor extracted from a sensor attached to a subject that has been selected for further analysis. The tremor comprises a series of tremor cycles 105, each tremor cycle comprising a periodic variation in the observed or sensed movement of the subject due to the tremor.

FIG. 1b shows the tremor signal of FIG. 1a, filtered between 2 and 9 Hz frequency and a zero-crossing threshold applied. This creates a filtered signal 110, comprising a plurality of filtered tremor cycles 115. From this filtered signal 110, the instantaneous period $T_n$ 120 can be calculated for each tremor cycle 115, and the corresponding instantaneous frequency $f_n = 1/T_n$. It is then possible to calculate the instantaneous variation of the frequency $\Delta f$ from one cycle n to the following n+1, ($\Delta f = f_n - f_{n+1}$).

Figure 2A:
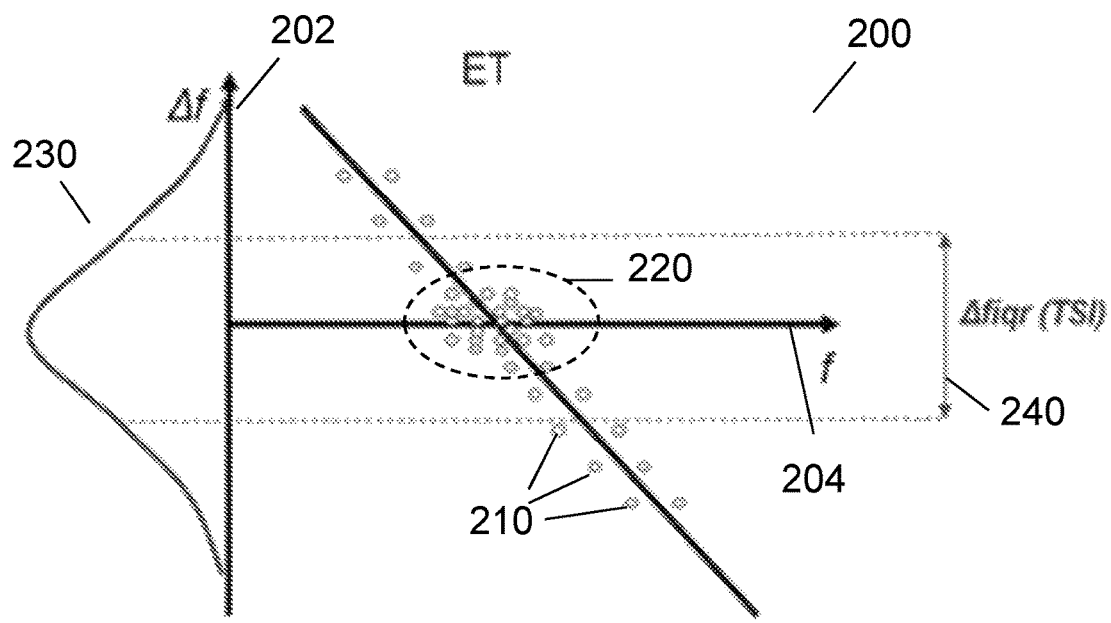
FIG. 2a shows a distribution of instantaneous frequency variation calculated from a or the filtered signal of FIG. 1b for a subject having an essential tremor.
Figure 2B:
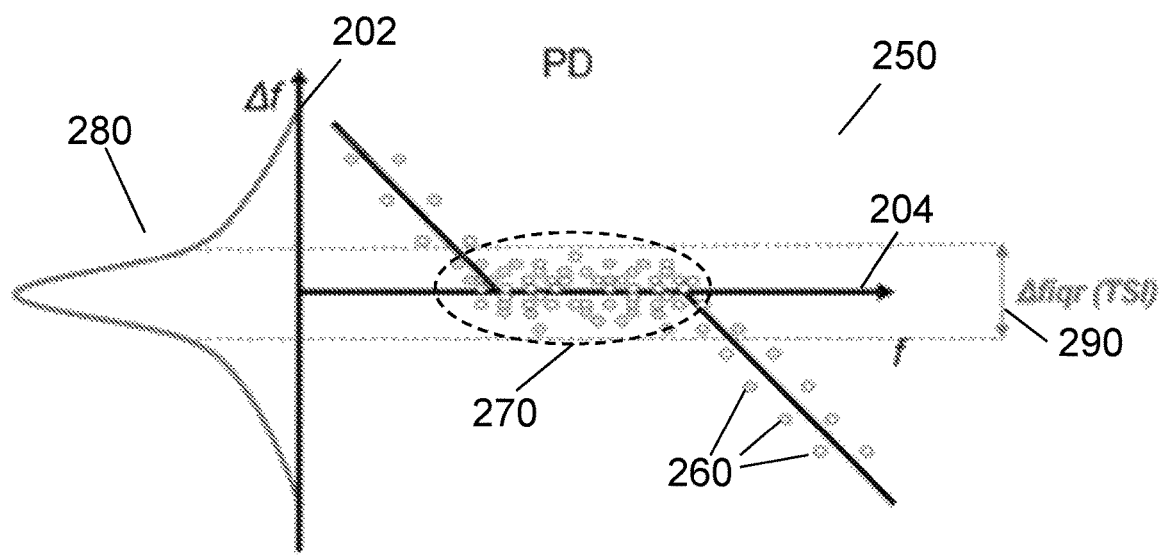
FIG. 2b shows a distribution of instantaneous frequency variation calculated from a or the filtered signal of FIG. 1b for a subject having Parkinsons disease that is used to determine an index value or tremor sensitivity index (TSI)

FIGS. 2a and 2b show the relationship between the instantaneous frequency variation and the instantaneous frequency for a subject having an Essential Tremor (ET) tremor status and Parkinson's disease tremor status.

FIG. 2a shows a plot 200 of the instantaneous variation of the frequency $\Delta f$ 202 as a function of the overall frequency, f 204 for a single subject selected from a cohort of subjects known to be suffering from essential tremor. FIG. 2a shows a series of data points 210 that correspond to the instantaneous variation $\Delta f$ at various instantaneous frequencies. A narrow band or grouping 220 is shown corresponding to a small instantaneous variation at a narrow band of frequencies. At higher or lower frequencies, the instantaneous variation between adjacent tremor cycles is larger. In other words, in essential tremor, only a small number of frequencies, centred about a single frequency, are stable. Away from this central single frequency, the frequency of the tremor varies from tremor cycle to tremor cycle.

A probability distribution 230 of the data points 210 can be determined. From this probability distribution, a band may be selected. In the example shown, the central interquartile range 240 is used to select the central two quartiles from the probability distribution 230. The width of this central interquartile range determines an index value, known as a tremor stability index 240.

FIG. 2b shows a second plot 250 of instantaneous variation of the frequency $\Delta f$ 202 as a function of the overall frequency, f 204 for a single subject selected from a cohort of subjects known to be suffering from Parkinson's disease. Again, as per FIG. 2a, a series of data points 260 that correspond to the instantaneous variation $\Delta f$ at various instantaneous frequencies is shown. A narrow band or grouping 270 is shown corresponding to a small instantaneous variation at a wider band of frequencies than in FIG. 2a. At higher or lower frequencies, the instantaneous variation between adjacent tremor cycles is larger. In other words, in Parkinson's disease, a larger number of frequencies, centred about a single frequency, are stable. Away from this central band of frequencies, the frequency of the tremor varies from tremor cycle to tremor cycle.

A probability distribution 280 of the data points 260 can be determined. From this probability distribution, a band may be selected. in the example shown the central interquartile range 290 is used to select the central two quartiles from the probability distribution 280. The width of this central interquartile range determines an index value, or tremor stability index 290 for the Parkinson's disease subject.

It can be appreciated that a comparison between FIGS. 2a and 2b shows that the probability density and associated tremor stability index values differ for a subject with essential tremor vs Parkinson's based tremor.

Materials and Methods

Patients

All patients gave informed consent and their study was approved by local research ethics committees in accordance with the Declaration of Helsinki. In each dataset, tremor data were collected after overnight withdrawal of anti-parkinsonian and anti-tremor medications, and after at least one hour of switching off any neurostimulation in patients implanted with Deep Brain Stimulation (DBS).

Data was divided in to two. A test dataset comprised two cohorts; the first composed of 16 rest tremor recordings of tremor-dominant PD patients from the University Campus Bio-Medico of Rome, Italy, and the second composed of postural tremor recordings in 20 ET patients from the University Hospital Cologne, Germany. A validation dataset comprised of data from four cohorts drawn from previously published studies (Table 1); cohort 3 of 9 PD and 8 ET tremor recordings; cohort 4 of 20 PD tremor recordings; cohort 5 of 6 PD tremor recordings, and cohort 6 of 7 PD tremor recordings. The patients in cohort 5 underwent DBS functional neurosurgery (neurosurgical targets: 2 patients VIM, 3 patients STN, 1 patient GPi). The patients in cohort 6 underwent STN DBS functional neurosurgery.

TABLE 1

Experiment 1 population's characteristics

| | Cohort Number | Diagnosis | Number of tremor recordings | Recording state | Age (mean ± std) | Disease duration (mean ± std) | Sensor type - Producer |
|---|---|---|---|---|---|---|---|
| Test Dataset | 1 | PD | 16 | Rest | 66.4 ± 8.6 | 6.7 ± 7.7 | Triaxial accelerometer - Opal sensor APDM, Inc. |
| | 2 | ET | 20 | Posture | 49.5 ± 15.5 | 24.3 ± 13.9 | Triaxial accelerometer - Brainvision acceleration sensor |

TABLE 1-continued

Experiment 1 population's characteristics

| | Cohort Number | Diagnosis | Number of tremor recordings | Recording state | Age (mean ± std) | Disease duration (mean ± std) | Sensor type - Producer |
|---|---|---|---|---|---|---|---|
| Validation Dataset | 3 | PD | 9 | Rest | 68.7 ± 8.2 | 6.5 ± 3.4 | Triaxial accelerometer - Biometrics. |
| | | ET | 8 | Posture | 68.6 ± 7.8 | 20.8 ± 19.4 | Triaxial accelerometer - Biometrics. |
| | 4 | PD | 20 | Rest | 68.2 ± 8.4 | 2.5 ± 2 | Triaxial accelerometer - Twente Medical Systems International - Biometrics - SomnoWatch |
| | 5 | PD | 6 | Rest | 58.5 ± 9.8 | 11.5 ± 5.3 | Velocity - transducing laser - Bruel and Kjaer, Naerum, Denmark |
| | 6 | PD | 7 | Rest | 49.5 ± 9.5 | 12.5 ± 6.8 | Triaxial accelerometer - Twente Medical Systems International |

The inclusion criteria for patients were the clinical diagnosis of PD or ET made by experienced movement disorders specialists following the Queen Square Brain Bank diagnostic criteria for PD patients and the criteria of the Consensus statement of the Movement Disorder Society on Tremor for ET patients. These clinical diagnoses also served as the diagnostic gold standard against which TSI was compared. In cohort 3 the clinical diagnoses were also supported by SPECT-DaTSCAN imaging. The same cohort had recordings demonstrating tremor at rest in both PD and ET patients, and was used to test the hypothesis that the TSI discriminates tremor types irrespective of postural context. The postural recordings manifesting tremor in ET patients in this cohort were further complemented by the collection of data in an additional seven PD patients who displayed reemergent postural tremor.

Tremor Recordings

Tremor recordings were made with a triaxial accelerometer, taped over the wrist in cohorts 1 and 2, over the middle finger or thumb in cohorts 3, 4 and 7, and over the dorsal surface of the hand in cohort 6. In cohort 5, index finger rest tremor was recorded with a velocity-transducing laser. In order to compare the same amount of data among patients, only 100 seconds of tremor recording was selected for analysis in each patient. To evaluate if the TSI value extracted from the surface EMG activity of wrist extensor and flexor muscles can differentiate PDT from ET, we also recorded EMG in cohort 3.

Data Analysis

The triaxial accelerometer data were trend corrected (0.1 Hz high-pass filtered) and the first principal component of the tremor extracted using principal component analysis (PCA) (MATLAB®, a proprietary multi-paradigm programming language and numeric computing environment developed by MathWorks®). This tremor component was then filtered between 2 and 9 Hz frequency. Signal to noise ratio (SNR) analysis was used to isolate and extract tremor data in PD re-emergent postural tremor (cohort 7).

As described above in relation to FIG. 1b, the instantaneous period $T_n$ was calculated for each tremor cycle in the extracted, filtered first principal component, and the corresponding instantaneous frequency $f_n=1/T_n$, by using a zero-crossing threshold on tremor data to define each tremor cycle. We than calculated the instantaneous variation of the frequency $\Delta f$ from one cycle n to the following n+1, ($\Delta f = f_n - f_{n+1}$).

The classification accuracy of TSI in the differential diagnosis of PDT and ET was assessed by binary logistic regression, using the enter method, and by receiver operating characteristic (ROC) curve analysis (IBM SPSS Statistics). The performance of TSI as a classifier was examined by calculating the sensitivity, specificity, accuracy, likelihood ratio positive, likelihood ratio negative and ROC area under the curve (AUC).

The TSI threshold for discriminating PD and ET was determined on the test dataset by selecting the cutoff which maximized the distance between sensitivity and (1-specificity). This corresponds to the threshold with the highest combination of sensitivity and specificity values. The potential cutoff values to be explored for their different diagnostic accuracy is limited to the number of the actual observations in the analysed dataset.

Results

Discriminating PDT and ET: Test Dataset.

Figure 3:
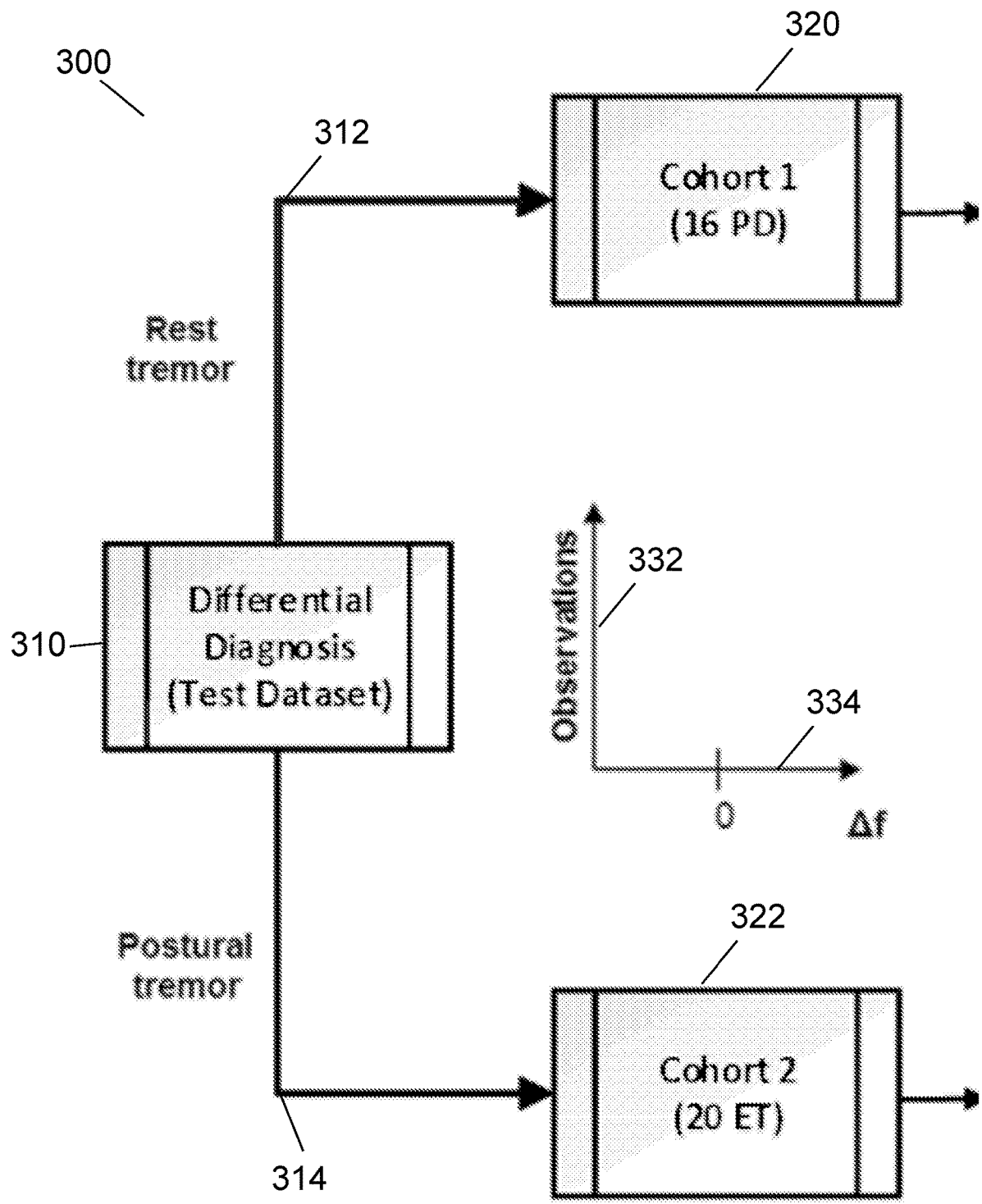
FIG. 3 shows the variation of distributions of FIGS. 2a and 2b for a cohort of subjects.
Figure 3:
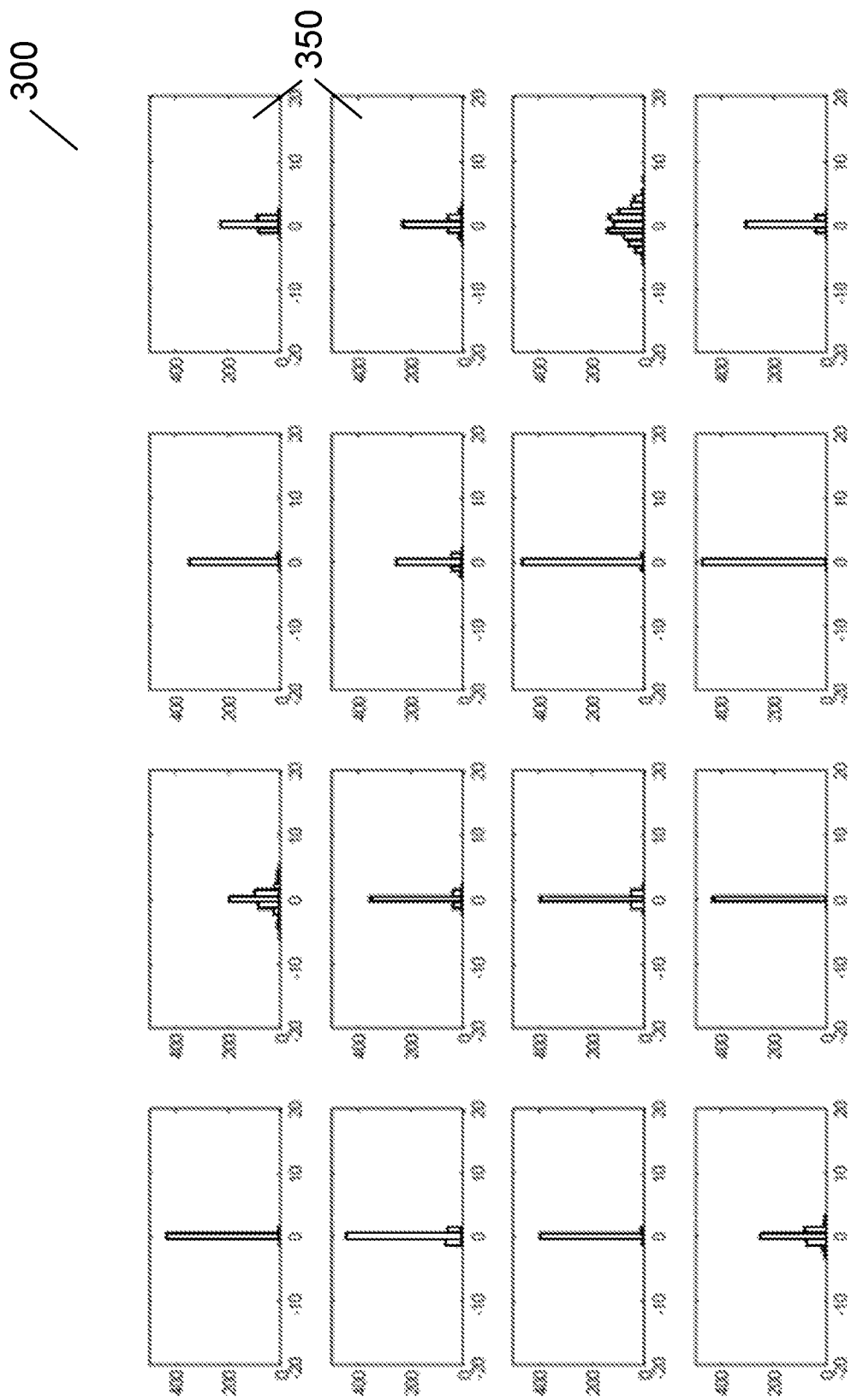
Figure 3:
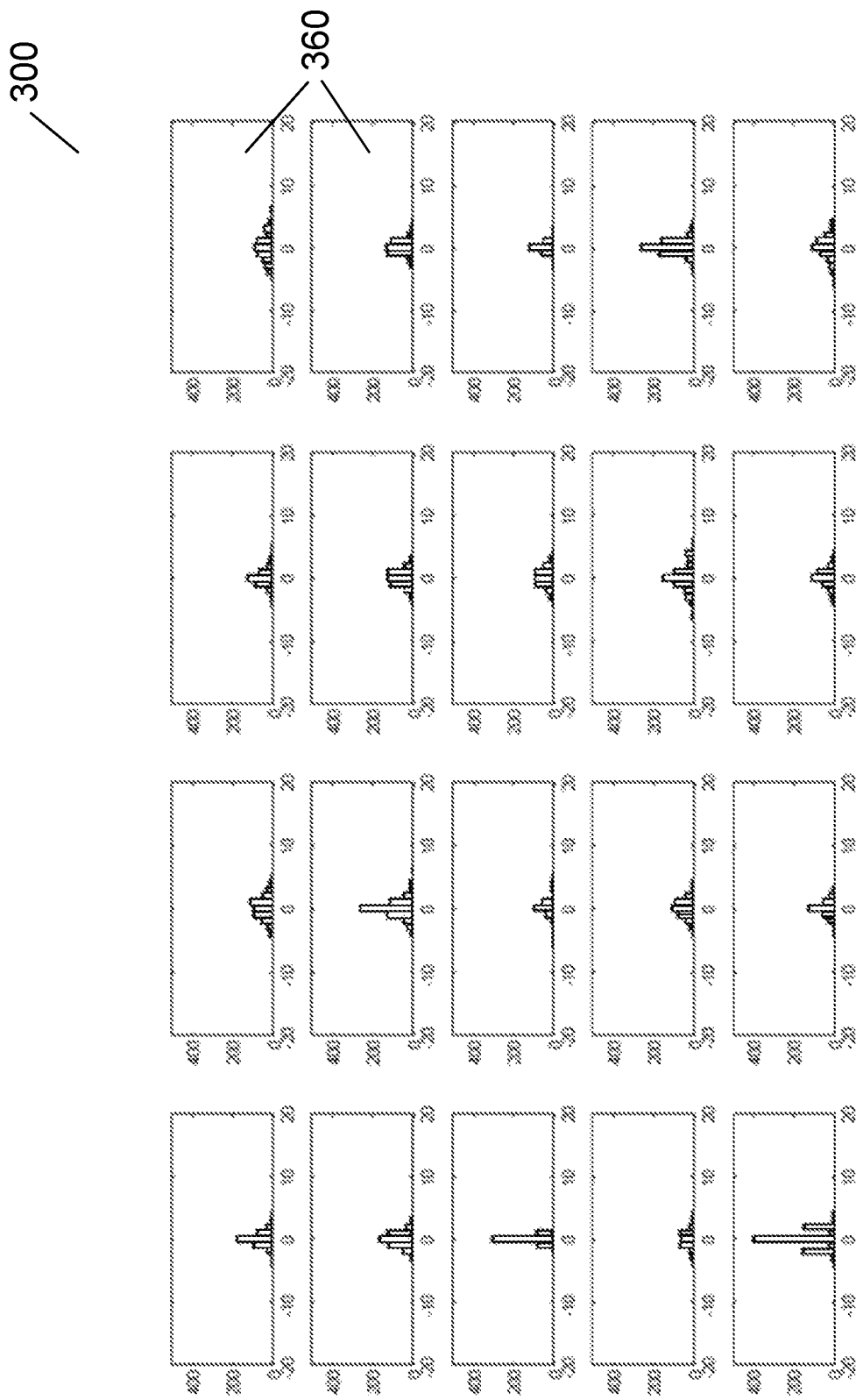

FIG. 3 shows a series of histogram plots 300 of the instantaneous variation of the frequency plotted against the Δf distribution for each patient in the test cohort. In particular, from a differential diagnosis 310, patients were divided into categories with rest tremor 312, indicative of PD and postural tremor 314 indicative of ET. This divided patients into two cohorts 320, 322. For each patient the observations 332 were plotted against the Δf distribution 334 as described above.

Patients with PD, shown in boxes 350, in whom tremor was recorded at rest, had a narrower and sharper Δf distribution than patients with ET, shown in boxes 360, recorded whilst they maintained a tremor provoking posture.

Figure 4:
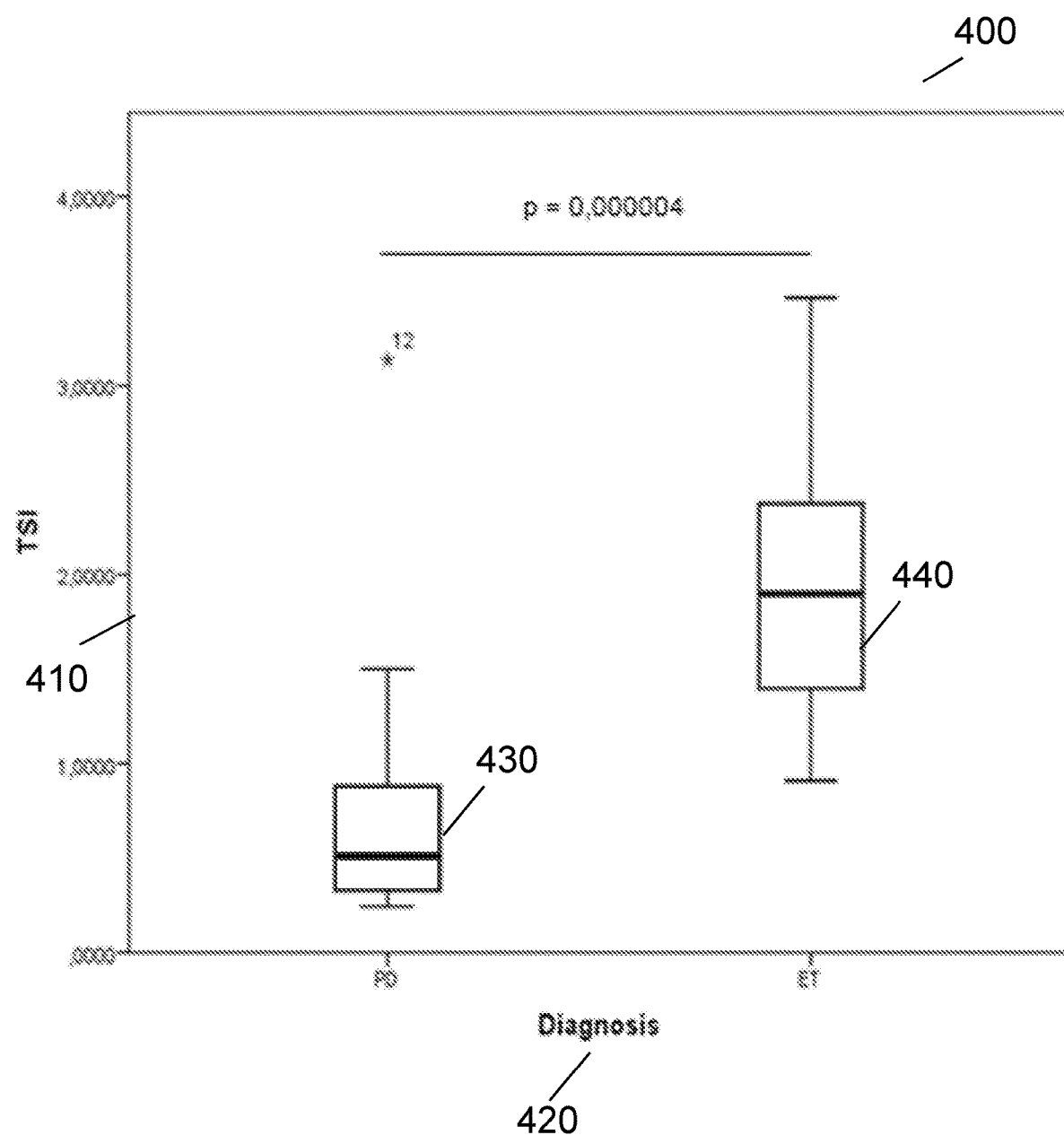
FIG. 4 is a boxplot of index values obtained from the distributions of FIG. 3.

To capture the difference in the distributions the Δf interquartile range was calculated, sometimes referred to as an index value and hereafter termed the Tremor stability index (TSI) in each group. This was different, with a mean TSI of 0.7±(SEM) 0.175 in PDT and of 1.9±0.134 in ET (t(34)=−5.481; p<0.001). This is shown in FIG. 4. This figure shows 400 TSI values 410 against known diagnosis 420. A diagnosis of PD tremor is shown in distribution 430, with essential tremor shown in 440.

Binary logistic regression showed that for every unit increase in TSI, the odds (Exp(B)) of a patient having a diagnosis of ET increased 14.8 times (95% C.I. for Exp(B) 2.9-75.1; p=0.001).

Figure 5:
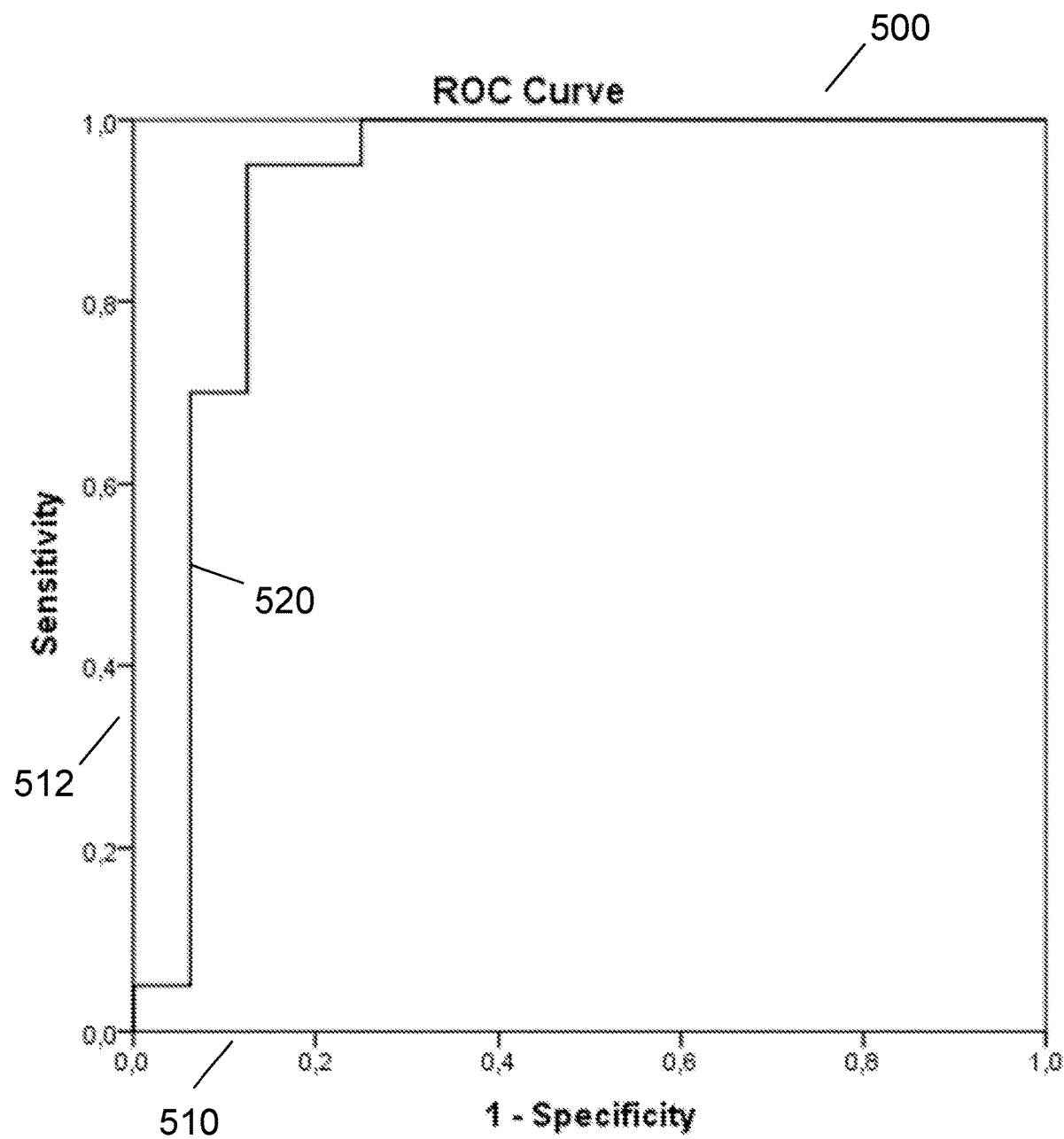
FIG. 5 is a receiver operating characteristic (ROC) curve of the index values of FIG. 4.

In addition, ROC curve analysis 500 of the TSI considering as a target a diagnosis of ET over PD is shown in FIG. 5 which compares the sensitivity 512 to the 1—specificity 510. The resultant plot 520 afforded an AUC of 0.916 (95% C.I. 0.797-1.000) with a standard error of 0.06.

Figure 6:
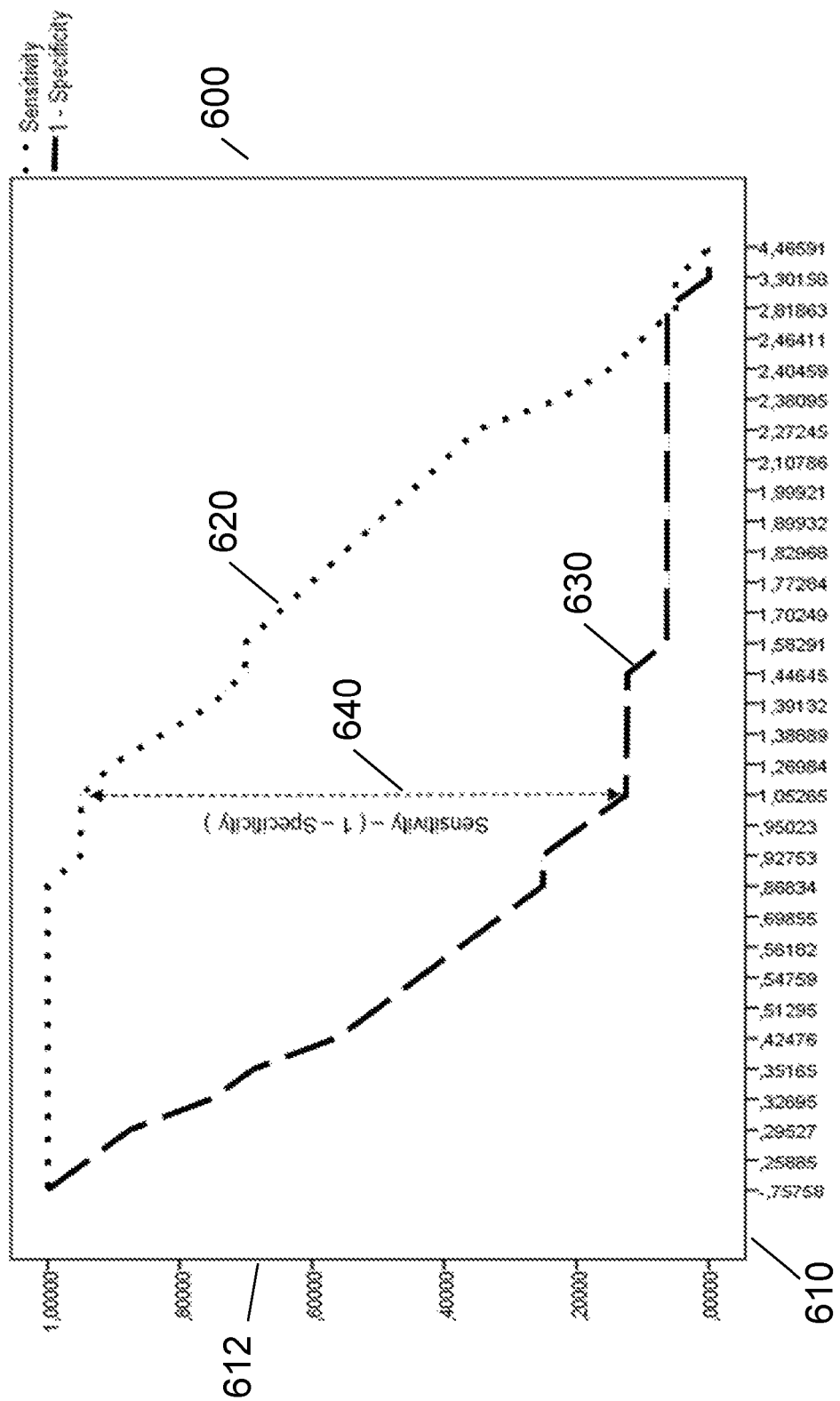
FIG. 6 is a sensitivity/specificity curve for various cutoff values of an index value.

To create FIG. 6 600 the lower and higher cutoff values were respectively, the minimum minus 1 and the maximum plus 1 observed values, and the cutoff values between these two extreme points were calculated by averaging two consecutively ordered observed values. Duplicated cutoffs were excluded from the analysis, leading to a total of 34 final potential cutoff points 610. The threshold 612 calculated from the test dataset was then used to verify the classification accuracy in the validation dataset, and in analyzing the effect of rest and posture.

Figure 7:
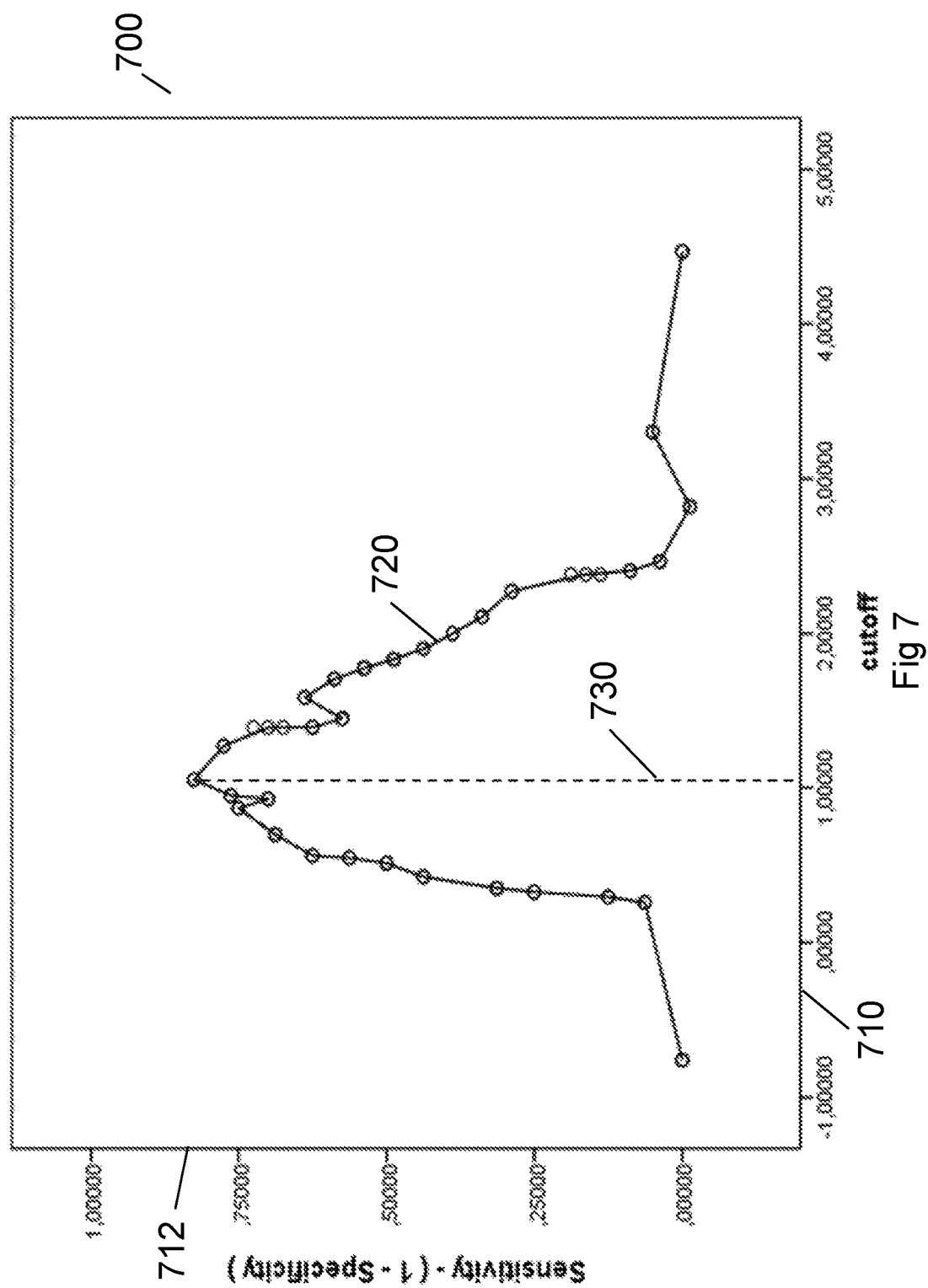
FIG. 7 is a sensitivity curve for different cutoff values.

To find the optimal TSI threshold for differentiating ET and PD a cutoff value of TSI was selected which maximized the distance 640 between sensitivity 620 and (1-specificity) 630, —the inputs to the ROC curve 500 above. This distance 640 corresponds to the threshold with the highest combination of sensitivity and specificity values (FIGS. 6 and 7). As shown in FIG. 7, 700, a comparison between the sensitivity 712 against the cutoff values 710, with the potential cutoff points 720 plotted, leads to a cutoff peak value of 1.05, 730.

This cutoff peak value is the optimal TSI threshold. TSI values >1.05 and ≤1.05 suggested a diagnosis of ET and PD, respectively. The diagnostic performance of this TSI threshold was excellent and is reported in Table 2.

TABLE 2

TSI diagnostic performance on test dataset.

| | Diagnosis | |
|---|---|---|
| | ET vs PD | PD vs ET |
| Sensitivity | 95% | 88% |
| Specificity | 88% | 95% |
| Accuracy | 92% | 92% |
| Likelihood ratio positive | 7.60 | 17.50 |
| Likelihood ratio negative | 0.06 | 0.13 |

Utility of the TSI Measure in Differentiating ET and PDT

To evaluate the minimum tremor recording duration needed for good classification accuracy, a bootstrapping technique was applied to the test dataset, by selecting 19 time lengths of 1 to 10 seconds in 1 second increments and 20 to 100 seconds in 10 second increments. 1000 iterations were performed.

Figure 8:
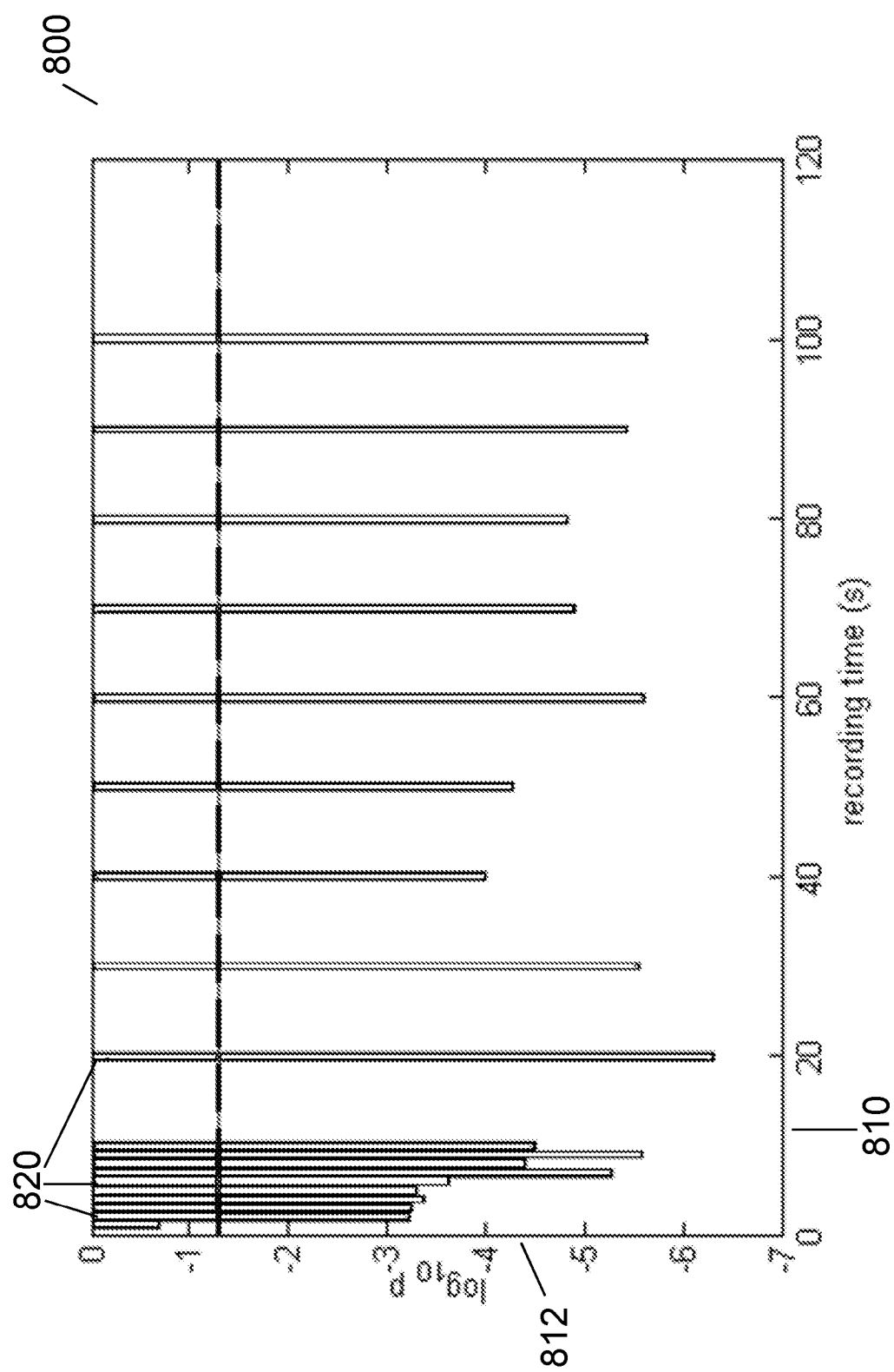
FIG. 8 is a logarithmic p-value curve against recording time.

Varies plots of recording durations are shown. In FIG. 8 800, the recording time 810 is compared to a logarithmic plot of the p-value 812. The resultant values 820 plotted in histogram format show that TSI can be used to distinguish between PDT and ET at times lower than 10 seconds duration.

Figure 9:
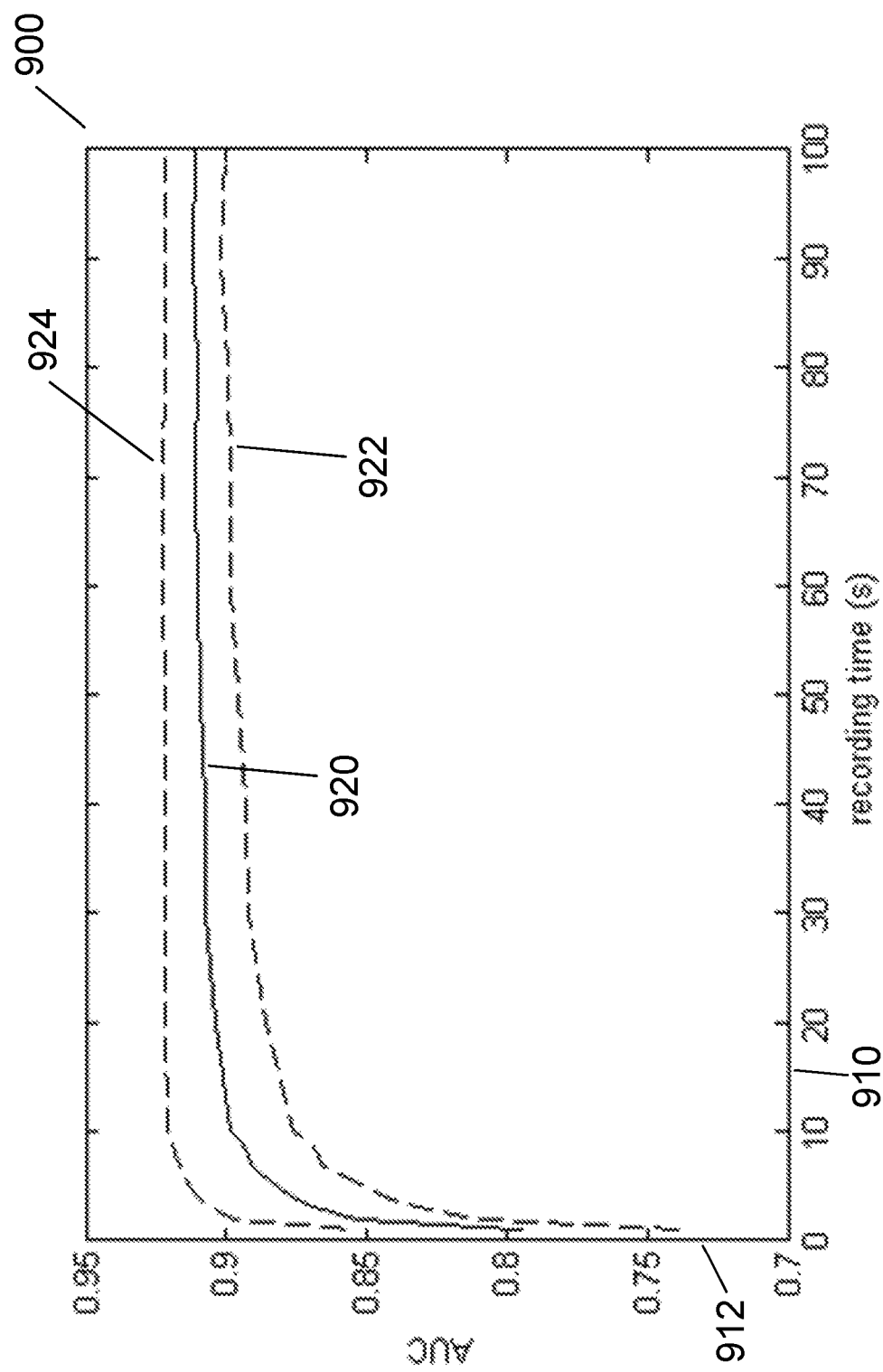
FIG. 9 is an area under the curve (AUC) value plot against recording time.

Having determined the diagnostic potential of TSI its utility and robustness were then explored. First, it was determined whether the TSI could be reliably estimated from clinically tractable tremor recording durations. Bootstrapping of recording durations showed that the TSI could help distinguish between PDT and ET with tremor recordings of as little as 2 seconds in duration (FIG. 8). The AUC 912 of the ROC curve 920 (with standard deviation confidence levels 922, 924) was 0.89 after as little as 10 seconds recording duration 910 (FIG. 9—900).

Figure 10:
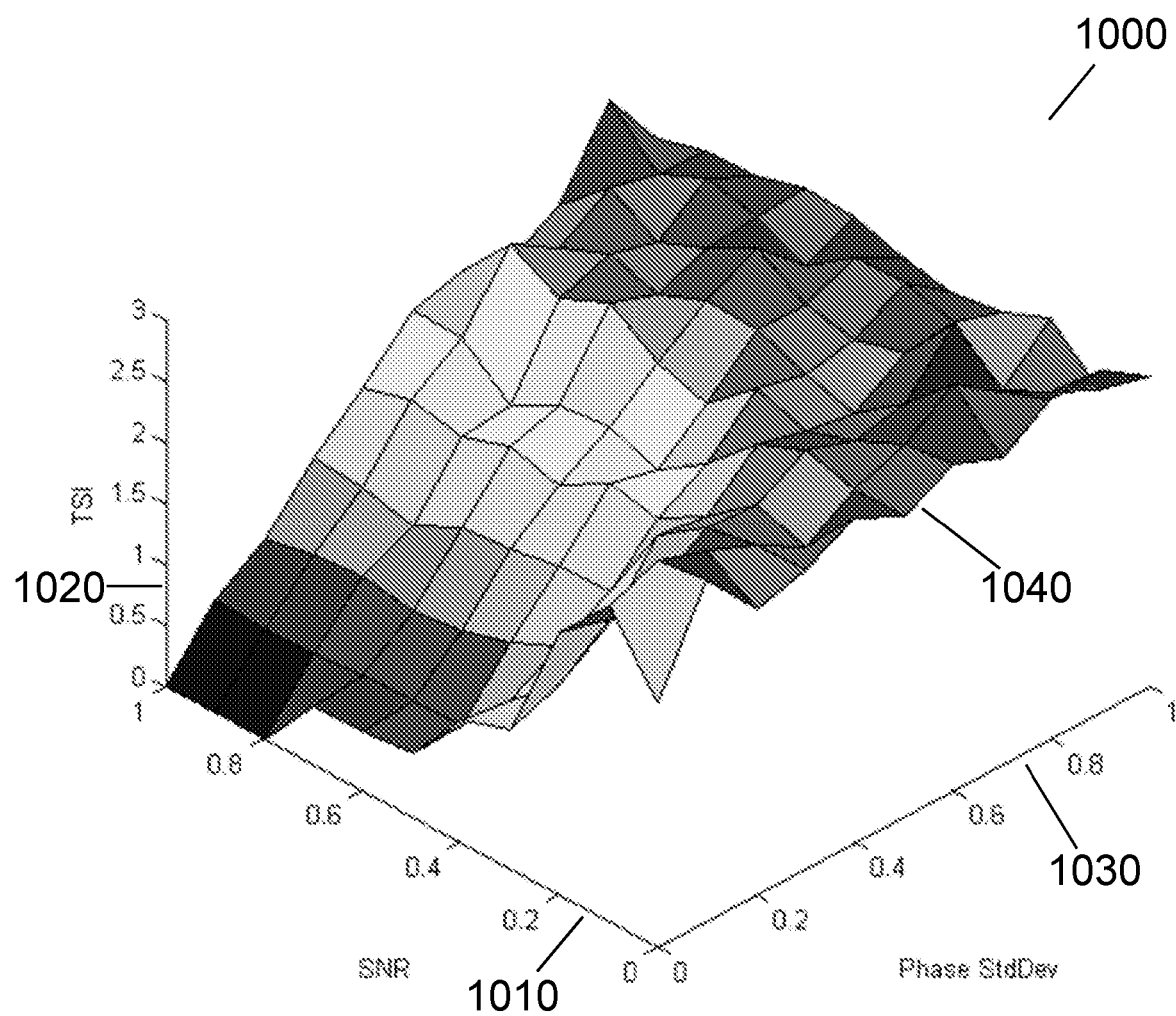
FIG. 10 is a plot of the sensitivity of the TSI to noise.

To evaluate the sensitivity of the TSI to tremor variability, the effect of two different types of signal noise, phase shifts and signal to noise ratio were simulated. This is shown in FIGS. 10—1000. The TSI 1020 increases linearly with increasing signal to noise ratio 1010 (SNR) and with the standard deviation of the tremor phase 1030 (Phase StdDev), only being zero in the case of a perfect sinusoid 1040 (with SNR=1 and Phase StdDev=0).

Lastly, it was examined if EMG could replace kinematic sensor data and maintain good discrimination. Comparison of the TSI value extracted from the surface EMG activity of the wrist extensor and flexor muscles in patients with PDT and ET in cohort 3 did not show any statistically significant difference (t(15)=−0.771; p=0.453) between the groups, with a mean TSI of 2.8±(SEM) 0.2 in PDT and of 3.1±0.09 in ET. This compares with the following TSI differences, (t(15)=−2.785; p=0.014), between the groups, mean TSI of 0.6±(SEM) 0.175 in PDT and of 1.6±0.134 in ET, calculated using accelerometer data in the same cohort.

Discriminating PDT and ET: Validation Dataset.

Figure 11:
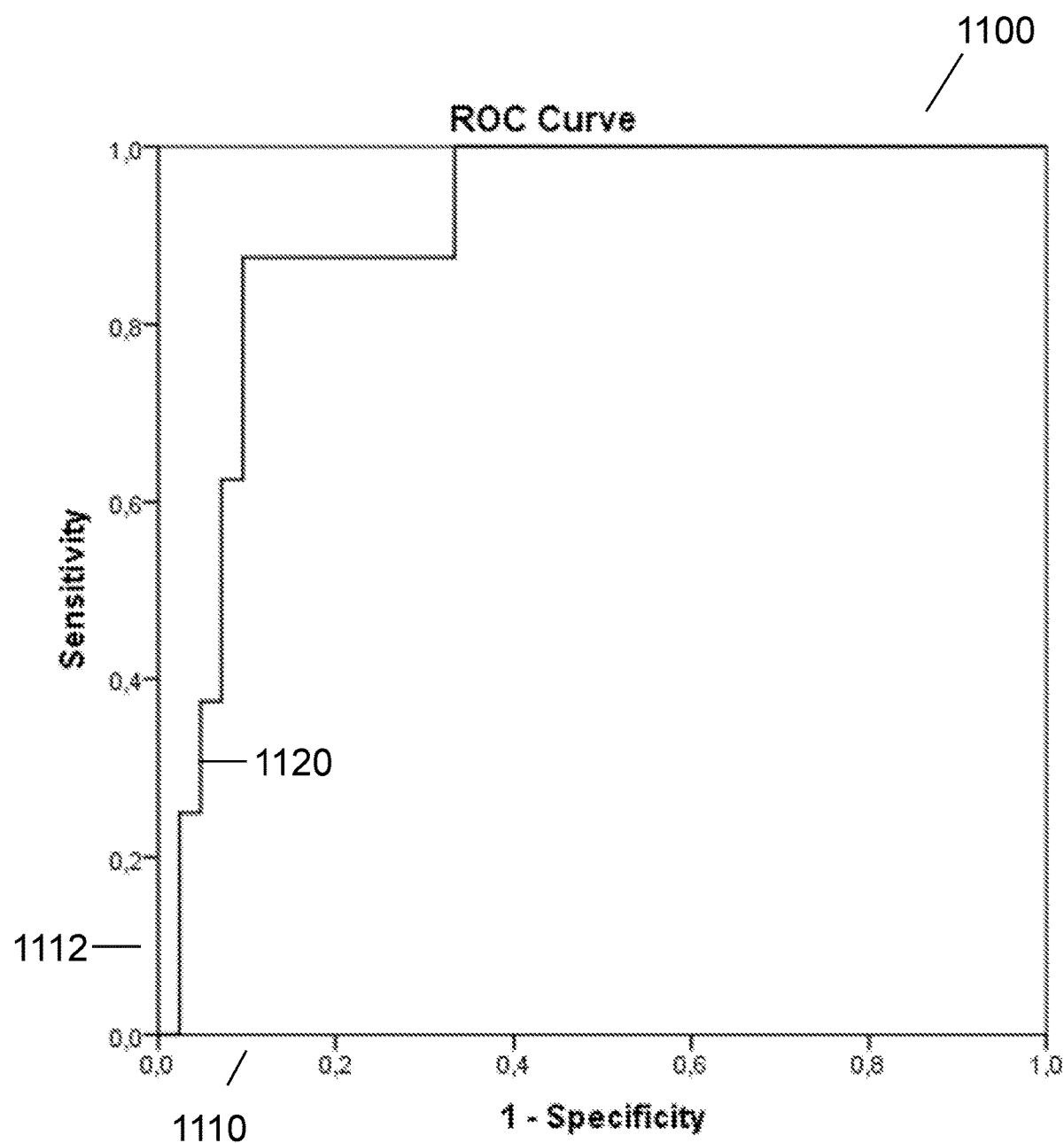
FIG. 11 is a ROC curve of the TSI as a diagnostic test.

For the validation dataset, a t-test confirmed a significant difference in the TSI in ET and PDT (TSI=0.5±(SEM) 0.125 in PD and 1.6±0.134 in ET patients; t(48)=−5.184; p<0.001). Binary logistic regression showed that for every unit increase in TSI, the odds (Exp(B)) of a patient having a diagnosis of ET increased 8.2 times (95% C.I. for Exp(B) 2.3-28.2; p=0.001). In addition, ROC curve analysis 1100 of the TSI considering as target a diagnosis ET over PDT afforded an AUC of 0.905 (95% C.I. 0.812-0.998) with a standard error of 0.047 (FIG. 11, which plots sensitivity 1112 against 1-specificity 1110 to generate a ROC curve 1120).

Applying the same TSI threshold as for the validation dataset excellent diagnostic performance was found in discriminating ET from PDT (Table 3). Note that diagnostic performance was maintained despite the variable tremor recording technique across the different cohorts making up the validation data set (Table 1).

TABLE 3

TSI diagnostic performance on validation dataset.

| | Diagnosis | |
|---|---|---|
| | ET vs PD | PD vs ET |
| Sensitivity | 88% | 90% |
| Specificity | 90% | 88% |
| Accuracy | 90% | 90% |

TABLE 3-continued

TSI diagnostic performance on validation dataset.

|  | Diagnosis | |
|---|---|---|
|  | ET vs PD | PD vs ET |
| Likelihood ratio positive | 9.19 | 7.24 |
| Likelihood ratio negative | 0.14 | 0.11 |

Discriminating PDT and ET: Is the Value of the TSI Independent of Posture?

In the above analyses rest tremor in PD was contrasted with postural tremor in ET, so that diagnostic utility might just relate to the discrimination of postural state rather than disease specific tremor characteristics. The TSI diagnostic accuracy in cohort 3 was evaluated where recordings of tremor at rest were available in 9 PD and 8 ET patients. A t-test confirmed a significant difference in the TSI in ET and PDT present at rest (TSI=0.7±(SEM) 0.175 in PD and 2.5±0.201 in ET patients; t(15)=−4.438; p<0.001). Binary logistic regression showed that for every unit increase in TSI, the odds (Exp(B)) of a patient having a diagnosis of ET increased 8.8 times (95% C.I. for Exp(B) 1.4-56.9; p=0.022). In addition, ROC curve analysis of the TSI considering as target a diagnosis ET over PDT afforded an AUC of 0.931 (95% C.I. 0.812-1.000) with a standard error of 0.06. The same TSI threshold as in the test dataset was applied and excellent diagnostic performance found, despite all analysed tremor being recorded at rest (Table 4).

TABLE 4

TSI diagnostic performance on rest trenor comparison.

|  | Diagnosis | |
|---|---|---|
|  | ET vs PD | PD vs ET |
| Sensitivity | 100% | 78% |
| Specificity | 78% | 100% |
| Accuracy | 88% | 88% |
| Likelihood ratio positive | 4.50 | Inf.* |
| Likelihood ratio negative | 0.00 | 0.22 |

*Since the Likelihood ratio positive is equal to sensitivity/(1 − specificity), and since the specificity in this case is 1, the resulting Likelihood ratio positive is infinite.

The TSI diagnostic accuracy was evaluated by differentiating reemergent postural PD tremor from postural ET tremor, comparing reemergent postural tremor of 7 PD patients from cohort 7, to postural ET tremor of 8 ET patients from cohort 3. A t-test confirmed a significant difference in the TSI in ET and PDT present at rest (TSI=0.3±(SEM) 0.075 in PD and 1.6±0.134 in ET; t(13)=−4.861; p<0.001). Binary logistic regression showed that for every unit increase in TSI, the odds (Exp(B)) of a patient having a diagnosis of ET increased 78.7 times (95% C.I. for Exp(B) 1.2-4931.3; p=0.039). In addition, ROC curve analysis of the TSI considering as target a diagnosis ET over PDT afforded an AUC of 0.982 (95% C.I. 0.927-1.000) with a standard error of 0.028. Again, the same TSI threshold as in the test dataset was applied and excellent diagnostic performance found, despite all analysed tremor being recorded during posture (Table 5).

TABLE 5

TSI diagnostic performance on postural trenor comparison.

|  | Diagnosis | |
|---|---|---|
|  | ET vs PD | PD vs ET |
| Sensitivity | 88% | 100% |
| Specificity | 100% | 88% |
| Accuracy | 93% | 93% |
| Likelihood ratio positive | Inf* | 8.00 |
| Likelihood ratio negative | 0.13 | 0.,00 |

*Since the Likelihood ratio positive is equal to sensitivity/(1 − specificity), and since the specificity in this case is 1, the resulting Likelihood ratio positive is infinite.

Given the reliability of the TSI index, its potential use as a diagnostic and/or analysis tool for tremor allows differing tremor statuses to be distinguished with reliability and accuracy using non-invasive techniques.

From reading the present disclosure, other variations and modifications will be apparent to the skilled person. Such variations and modifications may involve equivalent and other features which are already known in the art of tremor measurement, and which may be used instead of, or in addition to, features already described herein.

Although the appended claims are directed to particular combinations of features, it should be understood that the scope of the disclosure of the present invention also includes any novel feature or any novel combination of features disclosed herein either explicitly or implicitly or any generalisation thereof, whether or not it relates to the same invention as presently claimed in any claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The applicant hereby gives notice that new claims may be formulated to such features and/or combinations of such features during the prosecution of the present application or of any further application derived therefrom.

For the sake of completeness it is also stated that the term "comprising" does not exclude other elements or steps, the term "a" or "an" does not exclude a plurality, a single processor or other unit may fulfil the functions of several means recited in the claims and reference signs in the claims shall not be construed as limiting the scope of the claims.

The invention claimed is:
1. A computer-implemented method of characterising tremor stability in a subject, said subject having an involuntary tremor symptomatic of a neurological disorder, the method comprising:
 obtaining a tremor signal of measured tremor data of the subject;
 identifying a series of tremor cycles from the tremor signal of measured tremor data of the subject, said tremor cycles comprising periodic variation in movement of the subject due to the tremor;
 filtering the tremor signal between 2 and 9 Hz frequency, and applying a zero-crossing threshold to create a filtered signal comprising a plurality of filtered tremor cycles;
 determining an instantaneous frequency for each filtered tremor cycle and collating the instantaneous frequencies;

determining an instantaneous variation between the instantaneous frequencies of each pair of adjacent filtered tremor cycles within the series;

comparing the instantaneous variation to the collation of determined instantaneous frequencies to determine a distribution of instantaneous variations; and determining an index value of the distribution of the instantaneous variations, said index value defining the stability of the tremor and wherein the index value is an interquartile range of the distribution of the instantaneous variations.

2. A method as claimed in claim 1, wherein the measured tremor data is obtained using a triaxial accelerometer.

3. A method as claimed in claim 1, wherein the measured tremor data is obtained using a velocity-transducing laser.

4. A method as claimed in claim 1, wherein the measured tremor data is obtained using any device able to extract a frequency of oscillation of a tremor affected body part of the subject.

5. A method as claimed in claim 1, wherein the frequency of each tremor cycle is identified by:
determining a first principal component of the tremor.

6. A method as claimed in claim 5, wherein the first principal component is extracted using principal component analysis.

7. A method as claimed in claim 1, wherein the frequency of each tremor cycle is identified by:
trend correcting the tremor cycles using a high pass filter.

8. A method according to claim 1, wherein the instantaneous frequency of each tremor cycle is identified by determining an instantaneous period for each filtered tremor cycle, and wherein the instantaneous frequency is equal to the inverse of the instantaneous period.

9. A method according to claim 8, wherein the instantaneous period is determined by using the zero crossing threshold on a measured tremor to define each tremor cycle.

10. A method according to claim 1, further comprising:
comparing the index value with reference index values generated from subjects having a known tremor status.

11. A method according to claim 1, wherein the method further comprises:
measuring the tremor for a time period to determine measured tremor data, said time period being between 10s and 100s.

12. A computer-implemented method of determining a tremor status in a subject, said subject having an involuntary tremor symptomatic of a neurological disorder, the method comprising:
determining, using the method of method claim 1, an index value for the subject, said index value characterising the stability of the tremor;
comparing the index value to a database of known index values, said known index values being previously generated from subjects having a known tremor status; and
determining the tremor status of the subject based on the index value comparison.

13. A computer-implemented method of distinguishing tremor statuses of subjects from a cohort of subjects, said subjects having an involuntary tremor symptomatic of a neurological disorder, the method comprising:
determining, using the method of method claim 1, an index value for each subject, said index value characterising the stability of the tremor for each subject; and
identifying groupings of subjects based on their index value, wherein the groupings define separate tremor statuses.

14. A system for calculating a value indicative of a tremor stability of a subject having an involuntary tremor symptomatic of a neurological disorder, said system comprising:
a processor configured to:
receive a tremor signal comprising sensor data corresponding to measured tremor data of the subject, said measured tremor data comprising tremor cycles measuring periodic variation in movement of the subject due to the tremor;
filtering the tremor signal between 2 and 9 Hz frequency, and applying a zero-crossing threshold to create a filtered signal comprising a plurality of filtered tremor cycles;
determine instantaneous frequencies for filtered tremor cycles of the tremor;
calculate frequency variations between the filtered tremor cycles; and
determine an index value indicative of a distribution of the frequency variations with instantaneous frequency and wherein the index value is an interquartile range of the distribution of the frequency variations.

15. The system of claim 14, further comprising:
a database containing one or more reference index values generated from subjects having a known tremor status.

16. The system of claim 15, wherein the processor is further configured to compare the index value to the reference index values to diagnose the tremor status.

17. A computer-implemented method of analysing a series of tremor cycles to determine a tremor status, said method comprising the steps of:
analysing a tremor signal of a tremor series comprising a plurality of tremor cycles from a sensor measuring tremor data of a subject;
filtering the tremor signal between 2 and 9 Hz frequency, and applying a zero-crossing threshold to create a filtered signal comprising a plurality of filtered tremor cycles;
determining an instantaneous frequency for each filtered tremor cycle;
determining an instantaneous variation between the instantaneous frequencies of adjacent filtered tremor cycles within the series;
comparing the instantaneous variation to a range of determined instantaneous frequencies to determine a distribution of instantaneous variations; and
determining an index value of the distribution of the instantaneous variations, said index value defining a tremor status and wherein the index value is an interquartile range of the distribution of the instantaneous variations.

18. A computer-implemented method of collecting tremor information from a subject, said subject having an involuntary tremor symptomatic of a neurological disorder, the method comprising:
sensing a tremor in the subject;
measuring the tremor for a predefined time to generate a transient tremor signal;
identifying a series of tremor cycles from a signal of the measured tremor;
filtering the tremor signal between 2 and 9 Hz frequency, and applying a zero-crossing threshold to create a filtered signal comprising a plurality of filtered tremor cycles;
determining an instantaneous frequency for each filtered tremor cycle and collating the instantaneous frequencies;

determining an instantaneous variation between the instantaneous frequencies of each pair of adjacent filtered tremor cycles within the series;

comparing the instantaneous variation to the collation of determined instantaneous frequencies to determine a distribution of instantaneous variations; and determining an index value of the distribution of the instantaneous variations and wherein the index value is an interquartile range of the distribution of the instantaneous variations.

* * * * *